(12) United States Patent
Anex et al.

(10) Patent No.: US 8,152,477 B2
(45) Date of Patent: Apr. 10, 2012

(54) ELECTROKINETIC PUMP DESIGNS AND DRUG DELIVERY SYSTEMS

(75) Inventors: Deon Stafford Anex, Livermore, CA (US); Charles Martin Schwimmer, Los Gatos, CA (US); David Laurence Black, Los Gatos, CA (US); Richard Dean Rush, Belmont, CA (US); Michael James Gearhart, Fremont, CA (US)

(73) Assignee: Eksigent Technologies, LLC, Dublin, CA (US)

( * ) Notice: Subject to any disclaimer, the term of this patent is extended or adjusted under 35 U.S.C. 154(b) by 729 days.

(21) Appl. No.: 12/094,956

(22) PCT Filed: Nov. 22, 2006

(86) PCT No.: PCT/US2006/045313
§ 371 (c)(1),
(2), (4) Date: Jan. 6, 2009

(87) PCT Pub. No.: WO2007/062182
PCT Pub. Date: May 31, 2007

(65) Prior Publication Data
US 2009/0185916 A1 Jul. 23, 2009

Related U.S. Application Data

(60) Provisional application No. 60/739,390, filed on Nov. 23, 2005.

(51) Int. Cl.
*F04F 99/00* (2009.01)
*F01B 31/00* (2006.01)
*G01F 11/00* (2006.01)
*A61M 1/00* (2006.01)

(52) U.S. Cl. ........... 417/48; 91/422; 92/181 R; 222/309; 222/319; 222/340; 604/152

(58) Field of Classification Search .................... 91/422; 92/181 R; 222/309, 319, 340; 417/48, 379, 417/385; 604/151, 152
See application file for complete search history.

(56) References Cited

U.S. PATENT DOCUMENTS
1,063,204 A 6/1913 Kraft
(Continued)

FOREIGN PATENT DOCUMENTS
CN 2286429 Y 7/1998
(Continued)

OTHER PUBLICATIONS

PCT/US2006/045313, International Preliminary Report on Patentability and Written Opinion dated Sep. 13, 2007.

(Continued)

*Primary Examiner* — Nimeshkumar Patel
*Assistant Examiner* — Steven Horikoshi
(74) *Attorney, Agent, or Firm* — Shay Glenn LLP (57) ABSTRACT

One embodiment of the present invention provides a piston assembly having a piston housing filled with an electrolyte; a housing within the piston housing that divides the piston housing into a first portion and a second portion, the housing having apertures, a shaft connecting the housing to a piston head outside of the piston housing; and a porous material inside of the housing in contact with the electrolyte. Additionally, there are provided a method for filling the delivery chamber with a delivery fluid by withdrawing the piston head from within the delivery chamber. Yet another embodiment provides a method for filling a fluid delivery assembly by withdrawing a shaft from within the fluid delivery assembly to simultaneously displace a moving pump element within the delivery chamber and bypass fluid around a housing in the pump chamber.

16 Claims, 5 Drawing Sheets

U.S. PATENT DOCUMENTS

| | | | |
|---|---|---|---|
| 2,615,940 A | 10/1952 | Williams | |
| 2,644,900 A | 7/1953 | Hardway, Jr. | |
| 2,644,902 A | 7/1953 | Hardway, Jr. | |
| 2,661,430 A | 12/1953 | Hardway, Jr. | |
| 2,841,324 A | 7/1958 | Santeler | |
| 2,995,714 A | 8/1961 | Hannah | |
| 3,143,691 A | 8/1964 | Hurd | |
| 3,209,255 A | 9/1965 | Estes et al. | |
| 3,298,789 A | 1/1967 | Mast | |
| 3,427,978 A | 2/1969 | Hanneman et al. | |
| 3,544,237 A | 12/1970 | Walz | |
| 3,587,227 A * | 6/1971 | Weingarten | 60/326 |
| 3,630,957 A | 12/1971 | Rey et al. | |
| 3,682,239 A | 8/1972 | Abu-Romia | |
| 3,714,528 A | 1/1973 | Vail | |
| 3,739,573 A | 6/1973 | Giner | |
| 3,923,426 A | 12/1975 | Theeuwes | |
| 3,952,577 A | 4/1976 | Hayes et al. | |
| 4,043,895 A | 8/1977 | Gritzner | |
| 4,140,122 A | 2/1979 | Kuhl et al. | |
| 4,240,889 A | 12/1980 | Yoda et al. | |
| 4,383,265 A | 5/1983 | Kohashi | |
| 4,396,925 A | 8/1983 | Kohashi | |
| 4,402,817 A | 9/1983 | Maget | |
| 4,639,244 A | 1/1987 | Rizk et al. | |
| 4,687,424 A | 8/1987 | Heimes | |
| 4,704,324 A | 11/1987 | Davis et al. | |
| 4,789,801 A | 12/1988 | Lee | |
| 4,886,514 A | 12/1989 | Maget | |
| 4,908,112 A | 3/1990 | Pace | |
| 4,921,041 A | 5/1990 | Akachi | |
| 4,999,069 A | 3/1991 | Brackett et al. | |
| 5,004,543 A | 4/1991 | Pluskal et al. | |
| 5,037,457 A | 8/1991 | Goldsmith et al. | |
| 5,087,338 A | 2/1992 | Perry et al. | |
| 5,116,471 A | 5/1992 | Chien et al. | |
| 5,126,022 A | 6/1992 | Soane et al. | |
| 5,137,633 A | 8/1992 | Wang | |
| 5,219,020 A | 6/1993 | Akachi | |
| 5,260,855 A | 11/1993 | Kaschmitter et al. | |
| 5,296,115 A | 3/1994 | Rocklin et al. | |
| 5,351,164 A | 9/1994 | Grigortchak et al. | |
| 5,418,079 A | 5/1995 | Diethelm | |
| 5,531,575 A * | 7/1996 | Lin | 417/526 |
| 5,534,328 A | 7/1996 | Ashmead et al. | |
| 5,573,651 A | 11/1996 | Dasgupta et al. | |
| 5,581,438 A | 12/1996 | Halliop | |
| 5,628,890 A | 5/1997 | Carter et al. | |
| 5,632,876 A | 5/1997 | Zanzucchi et al. | |
| 5,658,355 A | 8/1997 | Cottevieille et al. | |
| 5,683,443 A | 11/1997 | Munshi et al. | |
| 5,766,435 A | 6/1998 | Liao et al. | |
| 5,858,193 A | 1/1999 | Zanzucchi et al. | |
| 5,862,035 A | 1/1999 | Farahmandi et al. | |
| 5,888,390 A | 3/1999 | Craig | |
| 5,891,097 A | 4/1999 | Saito et al. | |
| 5,942,093 A | 8/1999 | Rakestraw et al. | |
| 5,942,443 A | 8/1999 | Parce et al. | |
| 5,958,203 A | 9/1999 | Parce et al. | |
| RE36,350 E | 10/1999 | Swedberg et al. | |
| 5,961,800 A | 10/1999 | McBride et al. | |
| 5,964,997 A | 10/1999 | McBride | |
| 5,989,402 A | 11/1999 | Chow et al. | |
| 5,997,708 A | 12/1999 | Craig | |
| 6,007,690 A | 12/1999 | Nelson et al. | |
| 6,012,902 A | 1/2000 | Parce | |
| 6,013,164 A | 1/2000 | Paul et al. | |
| 6,019,882 A | 2/2000 | Paul et al. | |
| 6,045,933 A | 4/2000 | Okamoto | |
| 6,054,034 A | 4/2000 | Soane et al. | |
| 6,068,752 A | 5/2000 | Dubrow et al. | |
| 6,068,767 A | 5/2000 | Garguilo et al. | |
| 6,074,725 A | 6/2000 | Kennedy | |
| 6,086,243 A | 7/2000 | Paul et al. | |
| 6,090,251 A | 7/2000 | Sundberg et al. | |
| 6,100,107 A | 8/2000 | Lei et al. | |
| 6,106,685 A | 8/2000 | McBride et al. | |
| 6,113,766 A | 9/2000 | Steiner et al. | |
| 6,126,723 A | 10/2000 | Drost et al. | |
| 6,129,973 A | 10/2000 | Martin et al. | |
| 6,137,501 A | 10/2000 | Wen et al. | |
| 6,150,089 A | 11/2000 | Schwartz | |
| 6,156,273 A | 12/2000 | Regnier et al. | |
| 6,159,353 A | 12/2000 | West et al. | |
| 6,167,910 B1 | 1/2001 | Chow | |
| 6,176,962 B1 | 1/2001 | Soane et al. | |
| 6,210,986 B1 | 4/2001 | Arnold et al. | |
| 6,224,728 B1 | 5/2001 | Oborny et al. | |
| 6,238,538 B1 | 5/2001 | Parce et al. | |
| 6,255,551 B1 | 7/2001 | Shapiro et al. | |
| 6,257,844 B1 | 7/2001 | Stern | |
| 6,267,858 B1 | 7/2001 | Parce et al. | |
| 6,274,089 B1 | 8/2001 | Chow et al. | |
| 6,277,257 B1 | 8/2001 | Paul et al. | |
| 6,287,438 B1 | 9/2001 | Knoll | |
| 6,287,440 B1 | 9/2001 | Arnold et al. | |
| 6,290,909 B1 | 9/2001 | Paul et al. | |
| 6,319,476 B1 | 11/2001 | Victor, Jr. et al. | |
| 6,320,160 B1 | 11/2001 | Eidsnes et al. | |
| 6,344,120 B1 | 2/2002 | Haswell et al. | |
| 6,379,402 B1 | 4/2002 | Suhara et al. | |
| 6,406,605 B1 | 6/2002 | Moles | |
| 6,409,698 B1 | 6/2002 | Robinson et al. | |
| 6,418,966 B2 | 7/2002 | Loo | |
| 6,418,968 B1 | 7/2002 | Pezzuto et al. | |
| 6,444,150 B1 | 9/2002 | Arnold | |
| 6,460,420 B1 | 10/2002 | Paul et al. | |
| 6,472,443 B1 | 10/2002 | Shepodd | |
| 6,477,410 B1 | 11/2002 | Henley et al. | |
| 6,495,015 B1 | 12/2002 | Schoeniger et al. | |
| 6,529,377 B1 | 3/2003 | Somadder et al. | |
| 6,561,208 B1 | 5/2003 | O'Connor et al. | |
| 6,605,472 B1 | 8/2003 | Skinner et al. | |
| 6,619,925 B2 | 9/2003 | Ohkawa | |
| 6,620,625 B2 | 9/2003 | Wolk et al. | |
| 6,689,373 B2 | 2/2004 | Johnson et al. | |
| 6,709,559 B2 | 3/2004 | Sundberg et al. | |
| 6,719,535 B2 | 4/2004 | Rakestraw et al. | |
| 6,729,352 B2 | 5/2004 | O'Connor et al. | |
| 6,733,244 B1 | 5/2004 | Fritsch et al. | |
| 6,766,817 B2 | 7/2004 | da Silva | |
| 6,770,182 B1 | 8/2004 | Griffiths et al. | |
| 6,770,183 B1 | 8/2004 | Hencken et al. | |
| 6,814,859 B2 | 11/2004 | Koehler et al. | |
| 6,832,787 B1 | 12/2004 | Renzi | |
| 6,878,473 B2 | 4/2005 | Yamauchi et al. | |
| 6,918,404 B2 | 7/2005 | Dias da Silva | |
| 6,942,018 B2 | 9/2005 | Goodson et al. | |
| 6,952,962 B2 | 10/2005 | Hasselbrink et al. | |
| 6,994,151 B2 | 2/2006 | Zhou et al. | |
| 7,050,660 B2 | 5/2006 | Cyr et al. | |
| 7,094,464 B2 | 8/2006 | Mao et al. | |
| 7,101,947 B2 | 9/2006 | Schlenoff et al. | |
| 7,147,955 B2 | 12/2006 | Adams | |
| 7,217,351 B2 | 5/2007 | Krumme | |
| 7,235,164 B2 | 6/2007 | Anex et al. | |
| 7,258,777 B2 | 8/2007 | Paul et al. | |
| 7,267,753 B2 | 9/2007 | Anex et al. | |
| 7,364,647 B2 | 4/2008 | Paul et al. | |
| 7,399,398 B2 | 7/2008 | Rakestraw et al. | |
| 7,429,317 B2 | 9/2008 | Paul | |
| 7,517,440 B2 | 4/2009 | Anex et al. | |
| 7,521,140 B2 | 4/2009 | Arnold et al. | |
| 7,559,356 B2 | 7/2009 | Paul et al. | |
| 7,575,722 B2 | 8/2009 | Arnold | |
| 2001/0008212 A1 | 7/2001 | Shepodd et al. | |
| 2001/0052460 A1 | 12/2001 | Chien et al. | |
| 2002/0043805 A1 | 4/2002 | Charles et al. | |
| 2002/0048425 A1 | 4/2002 | McBride et al. | |
| 2002/0056639 A1 | 5/2002 | Lackritz et al. | |
| 2002/0066639 A1 | 6/2002 | Taylor et al. | |
| 2002/0070116 A1 | 6/2002 | Ohkawa | |
| 2002/0076598 A1 | 6/2002 | Bostaph et al. | |
| 2002/0089807 A1 | 7/2002 | Bluvstein et al. | |
| 2002/0125134 A1 | 9/2002 | Santiago et al. | |
| 2002/0166592 A1 | 11/2002 | Liu et al. | |
| 2002/0187074 A1 | 12/2002 | O'Connor et al. | |

| | | |
|---|---|---|
| 2002/0187197 A1 | 12/2002 | Caruso et al. |
| 2002/0187557 A1 | 12/2002 | Hobbs et al. |
| 2002/0189947 A1 | 12/2002 | Paul et al. |
| 2002/0195344 A1 | 12/2002 | Neyer et al. |
| 2003/0044669 A1 | 3/2003 | Hidaka et al. |
| 2003/0052007 A1 | 3/2003 | Paul et al. |
| 2003/0061687 A1 | 4/2003 | Hansen et al. |
| 2003/0116738 A1 | 6/2003 | O'Connor et al. |
| 2003/0138678 A1 | 7/2003 | Preidel |
| 2003/0173781 A1 | 9/2003 | Dodgson et al. |
| 2003/0190514 A1 | 10/2003 | Okada et al. |
| 2003/0198130 A1 | 10/2003 | Karp et al. |
| 2003/0198576 A1 | 10/2003 | Coyne et al. |
| 2003/0206806 A1 | 11/2003 | Paul et al. |
| 2003/0215686 A1 | 11/2003 | DeFilippis et al. |
| 2003/0226754 A1 | 12/2003 | Le Febre |
| 2003/0232203 A1 | 12/2003 | Mutlu et al. |
| 2004/0070116 A1 | 4/2004 | Kaiser et al. |
| 2004/0074768 A1* | 4/2004 | Anex et al. ............ 204/294 |
| 2004/0087033 A1 | 5/2004 | Schembri |
| 2004/0101421 A1 | 5/2004 | Kenny et al. |
| 2004/0106192 A1 | 6/2004 | Jeon et al. |
| 2004/0115731 A1 | 6/2004 | Hansen et al. |
| 2004/0118189 A1 | 6/2004 | Karp et al. |
| 2004/0129568 A1 | 7/2004 | Seul et al. |
| 2004/0163957 A1 | 8/2004 | Neyer et al. |
| 2004/0238052 A1 | 12/2004 | Karp et al. |
| 2004/0241004 A1 | 12/2004 | Goodson et al. |
| 2004/0241006 A1 | 12/2004 | Taboryski et al. |
| 2004/0247450 A1 | 12/2004 | Kutchinsky et al. |
| 2004/0248167 A1 | 12/2004 | Quake et al. |
| 2005/0161326 A1 | 7/2005 | Morita et al. |
| 2005/0166980 A1 | 8/2005 | Unger et al. |
| 2005/0252772 A1 | 11/2005 | Paul et al. |
| 2007/0066939 A1 | 3/2007 | Krulevitch et al. |
| 2007/0129792 A1 | 6/2007 | Picart et al. |
| 2007/0144909 A1 | 6/2007 | Anex et al. |
| 2007/0148014 A1 | 6/2007 | Anex et al. |
| 2007/0224055 A1 | 9/2007 | Anex et al. |
| 2008/0173545 A1 | 7/2008 | Anex et al. |
| 2008/0179188 A1 | 7/2008 | Nelson et al. |
| 2009/0148308 A1 | 6/2009 | Saleki et al. |
| 2011/0114492 A1 | 5/2011 | Anex et al. |

FOREIGN PATENT DOCUMENTS

| | | |
|---|---|---|
| DE | 1817719 A | 7/1970 |
| EP | 0421234 A2 | 4/1991 |
| EP | 1063204 A2 | 12/2000 |
| JP | H02-229531 | 9/1990 |
| JP | 03-087659 A | 4/1991 |
| JP | 07269971 A | 10/1995 |
| JP | 09270265 A | 10/1997 |
| JP | 02-265598 | 9/2002 |
| WO | WO 9405354 A1 * | 3/1994 |
| WO | WO 96/39252 A1 | 12/1996 |
| WO | WO 98/25065 A1 | 6/1998 |
| WO | WO 98/33001 A1 | 7/1998 |
| WO | WO 99/16162 A1 | 4/1999 |
| WO | WO 00/04832 A1 | 2/2000 |
| WO | WO 00/52376 A1 | 9/2000 |
| WO | WO 00/55502 A1 | 9/2000 |
| WO | WO 00/79131 A1 | 12/2000 |
| WO | WO 01/25138 A1 | 4/2001 |
| WO | WO 01/86155 A1 | 11/2001 |
| WO | WO 02/068821 A2 | 9/2002 |
| WO | WO02/070942 A1 | 9/2002 |
| WO | WO 02/086332 A1 | 10/2002 |
| WO | WO 2004/007348 A1 | 1/2004 |
| WO | WO2007062068 A3 | 5/2007 |
| WO | WO2007062182 A2 | 5/2007 |

OTHER PUBLICATIONS

PCT/US06/45112, International Search Report and Written Opinion dated Jan. 18, 2008.
Adamcyk et al., Characterization of Polyelectrolyte Multilayers by the Streaming Potential Method, Langmuir, 2004, vol. 20, 10517-10525.
Adamson et al., Physical Chemistry of Surfaces, pp. 185-187 (Wiley, NY 1997).
Ananthakrishnan et al., Laminar Dispersion in capillaries; A.I. Ch.E. Journal, 11(6):1063-1072 (Nov. 1965).
Aris, R.; On the dispersion of a solute in a fluid flowing through a tube. Proceedings of the Royal Society of London; Series A, Mathematical and Physical Sciences; vol. 235(1200); pp. 67-77; 1956.
Becker et al; Polymer microfabrication methods for microfluidic analytical applications; Electrophoresis; vol. 21; pp. 12-26; 2000.
Belfer et al.; Surface Modification of Commercial Polyamide Reverse Osmosis Membranes; J. Membrane Sci.; 139; pp. 175-181; 1998.
Bello et al; Electroosmosis of polymer solutions in fused silica capillaries; Electrophoresis; vol. 15; pp. 623-626; 1994.
Bings et al.; Microfluidic devices connected to fused-silica capillaries with minimal dead volume; Anal. Chem.; vol. 71; pp. 3292-3296 (1999).
Boerman et al.; Pretargeted radioimmunotherapy of cancer: progress step by step; J. Nucl. Med.; vol. 44; No. 3; pp. 400-411; Mar. 2003.
Boger, D.; Demonstration of upper and lower Newtonian fluid behaviour in a pseudoplastic fluid; Nature; vol. 265; pp. 126-128 (1977).
Braun et al.; Small-angle neutron scattering and cyclic voltammetry study on electrochemically oxidized and reduced pyrolytic carbon; Electrochimica Acta; vol. 49; pp. 1105-1112; 2004.
Buchholz et al.; Microchannel DNA sequencing matrices with switchable viscosities; Electrophoresis; vol. 23; pp. 1398-1409; 2002.
Burgreen et al.; Electrokinetic flow in ultrafine capillary slits; The Journal of Physical Chemistry, 68(95): pp. 1084-1091 (May 1964).
Chaiyasut et al.; Estimation of the dissociation constants for functional groups on modified and unmodified gel supports from the relationship between electroosmotic flow velocity and pH; Electrophoresis; vol. 22; pp. 1267-1272; 2001.
Chatwin et al.; The effect of aspect ratio on longitudinal diffusivity in rectangular channels; J. Fluid Mech.; vol. 120; pp. 347-358 (1982).
Collins, Kim; Charge density-dependent strength of hydration and biological structure; Biophys. J.; vol. 72; pp. 65-76; Jan. 1997.
Conway, B.E.; Electrochemical Supercapacitors Scientific Fundamentals and Technological Applications; Kluwer Academic/Plenum Publishers; pp. 12-13, pp. 104-105, and pp. 192-195; 1999.
Cooke Jr., Claude E.; Study of electrokinetic effects using sinusoidal pressure and voltage; The Journal of Chemical Physics; vol. 23; No. 12; pp. 2299-2300; Dec. 1955.
Dasgupta et al.; Electroosmosis: a reliable fluid propulsion system for flow injection analysis; Anal. Chem.; vol. 66; pp. 1792-1798; 1994.
Decher, Fuzzy Nanoassemblies: Toward Layers Polymeric Multicomposites, Science, 1997, vol. 277, pp. 1232-1237.
DeGENNES; Scaling Concepts in Polymer Physics; Cornell U. Press; p. 223; 1979.
Doshi et al.; Three dimensional laminar dispersion in open and closed rectangular conduits; Chemical Engineering Science, 33; pp. 795-804 (1978).
Drott et al.; Porous silicon as the carrier matrix in microstructured enzyme reactors yielding high enzyme activities; J. Micromech. Microeng; vol. 7; pp. 14-23 (1997).
Gan et al.; Mechanism of porous core electroosmotic pump flow injection system and its application to determination of chromium(VI) in waste-water; Talanta; vol. 51; pp. 667-675 (2000).
Gleiter et al.; Nanocrystalline Materials: A Way to Solids with Tunable Electronic Structures and Properties?; Acta Mater; 49; pp. 737-745; 2001.
Gongora-Rubio et al.; The utilization of low temperature co-fired ceramics (LTCC-ML) technology for meso-scale Ems, a simple thermistor based flow sensor; Sensors and Actuators; vol. 73; pp. 215-221; 1999.
Gonzalez et al.; Fluidic interconnects for modular assembly of chemical microsystems; Sensors and Actuators B; vol. 49; pp. 40-45 (1998).
Greene, George et al., Deposition and Wetting Characteristics of Polyelectrolyte Multilayers on Plasma-Modified Porous Polyethylene, Langmuir, 2004, vol. 20, pp. 2739-2745.

Gritsch et al.; Impedance Spectroscopy of Porin and Gramicidin Pores Reconstituted into Supported Lipid Bilayers on Indium-Tin-Oxide Electrodes; Langmuir; 14; pp. 3118-3125; 1998.

Gurau et al.; On the mechanism of the hofmeister effect; J. Am. Chem. Soc.; 2005; vol. 126; pp. 10522-10523.

Haisma; Direct Bonding in Patent Literature; Philips. J. Res.; vol. 49, pp. 165-170; 1995.

Hunter; Foundations of Colloid Science vol. II (Oxford Univ. Press, Oxford) pp. 994-1002; (1989).

Jackson, J. D.; Classical Electrodynamics 2nd Ed. John Wiley & Sons, Inc. New York. 1962.

Jacobasch et al.; Adsorption of ions onto polymer surfaces and its influence on zeta potential and adhesion phenomena, Colloid Polym Sci.; vol. 276: pp. 434-442 (1998).

Jarvis et al.; Fuel cell / electrochemical capacitor hybrid for intermittent high power applications; J. Power Sources; vol. 79; pp. 60-63; 1999.

Jenkins, Donald et al., Viscosity B-Coefficients of Ions in Solution, Chem. Rev. 1995, vol. 95, pp. 2695-2724.

Jessensky et al.; Self-organized formation of hexagonal pore structures in anodic alumina; J. Electrochem. Soc.; vol. 145; (11); pp. 3735-3740 (Nov. 1998).

Jimbo et al.; Surface Characterization of Poly(acrylonitrite) Membranes: Graft-Polymerized with Ionic Monomers as Revealed by Zeta Potential Measurements; Macromolecules; vol. 31; pp. 1277-1284; 1998.

Johnson et al.; Dependence of the conductivity of a porous medium on electrolyte conductivity; Physical Review Letters; 37(7); pp. 3502-3510 (Mar. 1, 1988).

Johnson et al.; New pore-size parameter characterizing transport in porous media; Physical Review Letter; 57(20); pp. 2564-2567 (Nov. 17, 1986).

Johnson et al.; Theory of dynamic permeability and tortuosity in fluid-saturated porous media; J. Fluid Mech; 176; pp. 379-402 (1987).

Jomaa et al., Salt-Induced Interdiffusion in Multilayers Films: A Neutron Reflectivity Study, Macromolecules; 2005, vol. 38, pp. 8473-8480.

Jones et al.; The viscosity of aqueous solutions of strong electrolytes with special reference to barium chloride; J. Am. Chem. Soc.; vol. 51; pp. 2950-2964; 1929.

Kiriy, Anton et al., Cascade of Coil-Globule Conformational Transitions of Single Flexible Polyelectrolyte Molecules in Poor Solvent, J. Am. Chem. Soc.; 2002, vol. 124, pp. 13454-13462.

Klein, F.; Affinity Membranes: a 10 Year Review; J. Membrance Sci.; vol. 179; pp. 1-27; 2000.

Kobatake et al.; Flows through charged membranes. I. flip-flop current vs voltage relation; J. Chem. Phys.; 40(8); pp. 2212-2218 (Apr. 1964).

Kobatake et al.; Flows through charged membranes. II. Oscillation phenomena; J. Chem. Phys.; 40(8); pp. 2219-2222 (Apr. 1964).

Kopf-Sill; Successes and challenges of lab-on-a-chip; Lab-on-a-Chip 2; pp. 42N-47N (2002).

Kotz et al.; Principles and applications of electrochemical capacitors; Electrochimica Acta; 45; pp. 2483-2498; 2000.

Liu et al.; Electroosmotically pumped capillary flow-injection analysis; Analytica Chimica Acta; vol. 283; pp. 739-745; 1993.

Liu et al.; Flow-injection analysis in the capillary format using electroosmotic pumping; Analytica Chimica Acta; vol. 268; pp. 1-6; 1992.

Ma et al.; A review of zeolite-like porous materials; Microporous and Mesoporous Materials; 37; pp. 243-252 (2000).

Manz et al.; Electroosmotic pumping and electrophoretic separations for miniaturized chemical analysis systems; J. Micromach. Microeng.; vol. 4; pp. 257-265; 1994.

Martin et al.; Laminated Plastic Microfluidic Components for Biological and Chemical Systems; J. Vac. Sci. Technol.; vol. A 17; pp. 2264-2269; 1999.

Mika et al., A new class of polyelectrolyte-filled microfiltration membranes with environmentally controlled porosity, Journal of Membrane Science; 1995, vol. 108, pp. 37-56.

Pretorius et al.; Electro-osmosis: a new concept for high-speed liquid chromatography; Journal of Chromatography; vol. 99; pp. 23-30; 1974.

Rastogi, R.P.; Irreversible thermodynamics of electro-osmotic effects; J. Scient. Ind. Res.; (28); pp. 284-292 (Aug. 1969).

Rice et al.; Electrokinetic flow in a narrow cylindrical capillary; J. Phys. Chem.; 69(11); pp. 4017-4024 (Nov. 1965).

Roberts et al.; UV Laser Machined Polymer Substrates for the Development of Microdiagnostic Systems; Anal. Chem.; vol. 69; pp. 2035-2042; 1997.

Rosen, M.J.; Ch.2—Adsorption of surface-active agents at interfaces: the electrical double layer; Surfactants and Interfacial Phenomena, Second Ed., John Wiley & Sons, pp. 32-107.

Salabat et al.; Thermodynamic and transport properties of aqueous trisodium citrate system at 298.15 K; J. Mol. Liq.; vol. 118; pp. 67-70; 2005.

Salomaeki et al., The Hofmeister Anion Effect and the Growth of Polyelectrolyte Multilayers, Langmuir; 2004, vol. 20, pp. 3679-3683.

Sankaranarayanan et al.; Chap. 1: Anatomical and pathological basis of visual inspection with acetic acid (VIA) and with Lugol's iodine (VILI); A Practical Manual on Visual Screening for Cervical Neoplasia; IARC Press; 2003.

Schmid et al.; Electrochemistry of capillary systems with narrow pores V. streaming potential: donnan hindrance of electrolyte transport; J. Membrane Sci.; 150; pp. 197-209 (1998).

Schmid, G.; Electrochemistry of capillary systems with narrow pores. II. Electroosmosis; J. Membrane Sci.; 150; pp. 159-170 (1998).

Schoenhoff, J.; Layered polyelectrolyte complexes: physics of formation and molecular properties, Journal of Physics Condensed Matter; 2003, vol. 15, pp. R1781-R1808.

Schweiss et al., Dissociation of Surface Functional Groups and Preferential Adsorption of Ions on Self-Assembled Monolayers Assessed by Streaming Potential and Streaming Current Measurements, Langmuir; 2001, vol. 17, pp. 4304-4311.

Stokes, V. K.; Joining Methods for Plastics and Plastic Composites: An Overview; Poly. Eng. and Sci.; vol. 29; pp. 1310-1324; 1989.

Takamura, Y., et al., "Low-Voltage Electroosmosis Pump and Its Application to On-Chip Linear Stepping Pneumatic Pressure Source," Abstract, Micro Total Analysis Systems, 2001, pp. 230-232.

Takata et al.; Modification of Transport Properties of Ion Exchange Membranes; J. Membrance. Sci.; vol. 179; pp. 101-107; 2000.

Taylor, G.; Dispersion of soluble matter in solvent flowing slowly through a tube; Prox. Roy. Soc. (London); 21; pp. 186-203; Mar. 31, 1953.

Tuckerman et al.; High-performance heat sinking for VLSI; IEEE Electron Dev. Letts., vol. EDL-2, pp. 126-129; May 1981.

Uhlig et al.; the electro-osmotic actuation of implantable insulin micropumps; Journal of Biomedical Materials Research; vol. 17; pp. 931-943; 1983.

Van Brunt, Jennifer; Armed antibodies; Signals (online magazine); 11 pgs.; Mar. 5, 2004.

Vinson, J.; Adhesive Bonding of Polymer Composites; Polymer Engineering and Science; vol. 29; No. 19; pp. 1325-1331; Oct. 1989.

Watson et al.; Recent Developments in Hot Plate Welding of Thermoplastics; Poly. Eng. and Sci.; vol. 29; pp. 1382-1386; 1989.

Weidenhammer, Petra et al., Investigation of Adhesion Properties of Polymer Materials by Atomic Force Microscopy and Zeta Potential Measurements, Journal of Colloid and Interface Science, vol. 180, pp. 232-236 (1996).

Weston et al.; Instrumentation for high-performance liquid chromatography; HPLC and CE, Principles and Practice, (Chp. 3) pp. 82-85, Academic Press.

Wijnhoven et al.; Preparation of photonic crystals made of air spheres in titania; Science; 281; pp. 802-804 (Aug. 7, 1998).

Wong et al., Swelling Behavior of Polyelectrolyte Multilayers in Saturated Water Vapor, Macromolecules; 2004, vol. 37, pp. 7285-7289.

Kou et al.; Surface modification of microporous polypropylene membranes by plasma-induced graft polyerization of ?-allyl glucoside; Langmuir; vol. 19; pp. 6869-6875; 2003.

Yazawa, T., Present status and future potential of preparation of porous glass and its application; Key Engineering Materials; 115; pp. 125-146 (1996).

Ye et al.; Capillary electrochromatography with a silica column with dynamically modified cationic surfactant; Journal of Chromatography A; vol. 855; pp. 137-145; 1999.

Yoo et al., Controlling Bilayer Composition and Surface Wettability of Sequentially Adsorbed Multilayers of Weak Polyelectrolytes, Macromolecules; 1998, vol. 31, pp. 4309-4318.

Zeng, S. et al., "Fabrication and characterization of electroosmotic micropumps," Sensors and Actuators, B 79: pp. 107-114 (2001).

Zhang et al.; Specific ion effects on the water solubility of macromolecules: PNIPAM and the Hofmeister series; J. Am. Chem. Soc.; vol. 127; pp. 14505-14510; 2005.

Anex et al.; U.S. Appl. No. 12/728,844 entitled "Electrokinetic Pump Designs and Drug Delivery Systems," filed Mar. 22, 2010.

Caruso et al.; Investigation of electrostatic interactions in polyelectrolyte multilayer fills: binding of anionic fluorescent probes to layers assemble onto colloids; Macromolecules; vol. 32; pp. 2317-2328 (1999).

Losche et al., Detailed structure of molecularly thin polyelectrolyte multilayer films on solid substrates as revealed by neutron reflectometry; Macromolecules; 1998; vol. 31; pp. 8893-8906.

Schlenoff et al., Mechanism of polyelectrolyte multilayer growth: charge overcompensation and distribution; Macromolecules; 2002, vol. 34, pp. 592-598.

Tusek et al.; Surface characterisation of NH3 plasma treated polyamide 6 foils; Colloids and Surfaces A; vol. 195; pp. 81-95; 2001.

Yezek; Bulk conductivity of soft surface layers: experimental measurement and electrokinetic implications; Langmuir; 2005; vol. 21; pp. 10054-10060.

Conway, B.E.; Electrochemical Capacitors Their Nature, Function, and Applications; Electrochemistry Encyclopedia. 2003. (Available at http://electrochem.cwru.edu/ed/encycl/art-c03-elchem-cap.htm. Accessed May 16, 2006).

Li et al., Studies on preparation and performances of carbon aerogel electrodes for the application of supercapacitor; Journal of Power Sources; vol. 158; pp. 784-788; 2006.

Krasemann et al.; Self-assembled polyelectrolyte multilayer membranes with highly improved pervaporation separation of ethanol/water mixtures; J of Membrane Science; vol. 181; No. 2; pp. 221-228; 2001.

\* cited by examiner

ELECTROKINETIC PUMP DESIGNS AND DRUG DELIVERY SYSTEMS

CROSS-REFERENCE TO RELATED APPLICATIONS

This application is the U.S. national stage of International Application No. PCT/US2006/045313, filed Nov. 22, 2006, and claims the benefit of U.S. Provisional Application No. 60/739,390 filed Nov. 23, 2005, titled, "Electrokinetic Pump Designs and Drug Delivery Systems," which is incorporated herein by reference in its entirety. This application is related to the following co-pending patent applications: U.S. Application Ser. No. 11/603,925 filed Nov. 22, 2006 and titled, "Electrokinetic Pump Designs and Drug Delivery Systems"; U.S. application Ser. No. 11/603,926 filed Nov. 22, 2006 and titled "Electrokinetic Pump Designs and Drug Delivery Systems"; U.S. application Ser. No. 10/198,223, filed Jul. 17, 2002 titled, "Laminated Flow Devices"; U.S. application Ser. No. 10/273,723 filed Oct. 18, 2002 titled, "Electrokinetic Device Having Capacitive Electrodes"; U.S. application Ser. No. 10/322,083 filed Dec. 17, 2002 titled, "Electrokinetic Device Having Capacitive Electrodes" and U.S. application Ser. No. 11/112,867 filed Apr. 21, 2005 titled, "Electrokinetic Delivery Systems, Devices and Methods," each of which are incorporated herein by reference in its entirety.

BACKGROUND OF THE INVENTION

Pumps and pumping systems exist for the delivery of various fluids. A variety of pumps are used in a number of various different configurations and uses. Pumps are used for infusion of drugs or delivery of drugs into mammals, the sterility of the drugs is very important. In addition, contamination of the drug or delivery fluid from the pump system should be reduced or eliminated. Additionally, it remains an important aspect to minimize contact between the drug to be delivered and the internal components of the pump being used to deliver the drug. Filling or preparing the drug or fluid for delivery should not be time consuming. These and other difficulties are encountered using conventional filling and pumping systems.

Related U.S. application Ser. No. 11/112,867 filed Apr. 21, 2005 titled, "Electrokinetic Delivery Systems, Devices and Methods," discloses a technique for filling a pump with fluid for delivery. This technique involves operating the pump system in reverse to draw the delivery fluid into the pump. Then, after filling the pump with the delivery fluid, the pump direction is reversed and the delivery fluid is delivered from the pump. Reversing pump direction may be a good solution for small amounts of fluid or for pump configurations that have a very high linear flow rate. However, the time requirements for loading large volumes of delivery fluid using this technique may be prohibitive for time conscious applications and problematic for later pump operation.

What are needed are improved techniques for providing the delivery fluid into the pumping system. The pump filling procedures should be simple and require small amounts of time.

SUMMARY OF THE INVENTION

One embodiment of the present invention provides a piston assembly having a piston housing; a housing within the piston housing that divides the piston housing into a first portion and a second portion, the housing having apertures that provide fluid communication between the first portion and the second portion; a shaft connecting the housing to a piston head outside of the piston housing; and a porous material inside of the housing. In one aspect, the piston housing is filled with an electrolyte. In another aspect, the porous material inside of the housing is in contact with the electrolyte.

In one aspect, the porous material is a porous dielectric material adapted for operation as part of an electrokinetic pump. In another aspect, there is a sealing element around the piston head or the housing. In yet another aspect, there is a second shaft connecting the housing to a handle outside of the piston housing. In another aspect there is a valve within the second shaft wherein actuation of the valve provides a flow path between the first portion and the second portion. In yet another aspect, the flow path from one side of the housing to the other side of the housing includes a bypass through the porous material contained in the housing. In another aspect, the valve is actuatable from a handle attached to the second shaft. In another aspect, the shaft extends through a wall in the piston housing. In another aspect, the sealing element around the material housing seals the housing to a wall of the piston housing. In another aspect, there is an electrode in the first portion and an electrode in the second portion. In one embodiment, the electrodes have a double layer capacitance of greater than $10^{-4}$ microfarad/cm$^2$.

In another embodiment of the invention, there is provided a pump having a delivery chamber, a pump chamber and a wall separating the pump chamber from the delivery chamber; a piston assembly having a piston head in the delivery chamber, a housing in the pump chamber and a shaft connecting the piston head to the housing and passing through the wall separating the pump chamber from the delivery chamber; and a dielectric material in the housing.

In one aspect, there is a pair of electrodes in the pump housing. In one aspect, there is one electrode is on each side of the housing. In one embodiment, the pair of electrodes are made from a material selected to electrokineticly move a fluid in the pump chamber. In one aspect, the delivery chamber and the pump chamber are in a single housing. In another aspect, the housing divides the pump chamber into a first portion and a second portion. In yet another aspect, there is provided apertures in the housing that provide fluid communication between the first portion and the second portion. In another aspect, there is an electrolyte in the pump chamber. In a further aspect, each electrode in the pair of electrodes has a double layer capacitance of more than $10^{-4}$ microfarad/cm$^2$. In yet another aspect, there is a bypass valve in the shaft that provides a fluid pathway from one side of the housing to the other side of the housing. In one aspect, the bypass valve in the shaft that provides a fluid pathway from the first portion to the second portion. In another aspect, the delivery chamber is filled with a delivery fluid by relative movement between the pump chamber and the delivery chamber. In another aspect, application of an electric field across the electrodes moves the fluid in the pump chamber from one side of the housing to the other side of the housing. In one aspect, application of an electric field across the electrodes moves the piston head in the delivery chamber. In another aspect, application of an electric field across the electrodes moves the housing relative to the pump chamber.

In another embodiment, there is provided a method for operating a fluid delivery system by inserting a piston assembly into a delivery chamber, the piston assembly having a pump housing, a piston head outside of the pump housing and attached to a shaft extending through a wall in the pump housing, a housing attached to the shaft and between electrodes in the pump housing; and filling the delivery chamber with a delivery fluid by withdrawing the piston head from within the delivery chamber. In one further aspect, the method fixes the position of the pump housing relative to the delivery chamber. In another aspect, there is provided the step of advancing the piston head in the delivery chamber by moving fluid in the pump chamber. In one aspect, moving fluid within the pump chamber comprises electrokineticly moving fluid through the housing. In another aspect, moving fluid within the pump chamber comprises providing an electric field between the electrodes. In yet another aspect, the filling step comprises withdrawing the pump assembly.

In another embodiment, there is a method for operating a fluid delivery assembly having a pump chamber and a delivery chamber by withdrawing a shaft from within the fluid delivery assembly to simultaneously displace a moving pump element within the delivery chamber and bypass fluid around a housing in the pump chamber.

In one aspect, withdrawing a shaft from the pump assembly introduces a delivery fluid into the delivery chamber and into contact with the moving pump element. In another aspect, advancing the moving pump element in the delivery chamber by applying an electrical field across electrodes in the pump chamber and on either side of the housing. Still another aspect provides electrokineticly moving fluid in the pump chamber to dispense fluid from the delivery chamber. In still another aspect includes actuating a bypass in the shaft during the withdrawing step.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS the novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figures 1A, 1B:
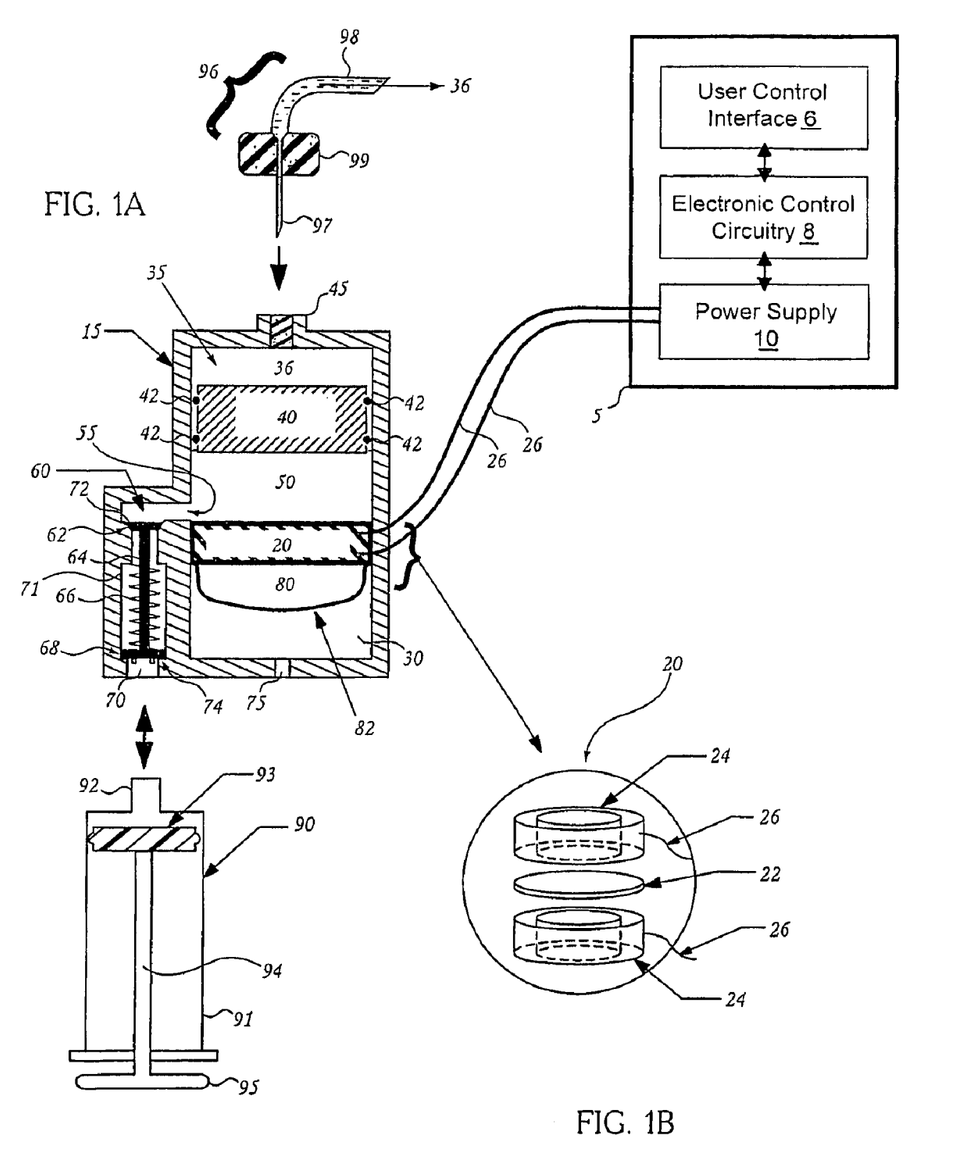
FIG. 1A is section view of an exemplary pump system.
FIG. 1B is an exploded view of a flow-through pump element of FIG. 1A.

FIGS. 1A and 1B will be described to provide an understanding of the basic components and operation of a typical fluid delivery system. FIG. 1A illustrates a cross section view of a fluid delivery system 1. The fluid delivery system has a first chamber 30, a second chamber 32 and a third chamber 35. A flow through pump element 20 (such as electrokinetic pump, as shown in FIG. 1B) separates the first chamber 30 from the second chamber 32. A moveable pump element 40 (such as a floating piston, as shown) separates the second chamber 32 from the third chamber 35. While in this illustrative embodiment the moveable element 40 is a floating piston, any device that provides a moveable barrier may be used as will be illustrated in the examples that follow. In this embodiment, the first, the second and the third chambers are within a single housing 15. Seals 42 are used to seal the moveable pump element 40 as it moves within the housing 15. An outlet 45 provides communication between the third chamber 35 and the exterior of housing 15. An outlet 55 provides communication between the second chamber 32 and the exterior of housing 15. In this embodiment, a valve 60 separates the second outlet 55 from the exterior of housing 15.

As illustrated, a conduit 71 connects the outlet 55 to the opening 70. A valve 60 in the conduit 71 controls fluid flow from the outlet 55 to the opening 70. The valve 60 has a disc 62, stem 64, a spring 66 and a disc or seal 68. Seats 72, 74 in the housing are shaped to seal with, respectively, discs or seals 62, 68. Valve 60 is shown in the closed position where spring 66 holds discs 68, 62 in place against seats 72, 74. In this embodiment, conduit 71 and valve 60 are disposed in a wall of housing 15. Other configurations are possible such as a separate valve assembly that attaches directly to port 55 or a valve/conduit configuration that ports through the pump element 20 rather than around the pump element 20 as shown.

In the illustrated embodiment, the first chamber 30 contains a moveable pump element 82 (i.e., a diaphragm adjacent the pump element 20). The first chamber 30 also contains a vent 75, if needed to ensure free movement of the moveable element 82. The space between the diaphragm 82 and the pump element 20 contains a buffer or pump fluid 80 that is selected to operate with the type of pump element used. If the pump element 20 is an electrokinetic pump, then the buffer 80 would be an electrolyte selected to operate with the electrode and porous material materials and desired operation of the pump. Examples of specific electrolytes and other details of electrokinetic pumps are described in co-pending and commonly assigned patent application serial numbers U.S. application Ser. No. 10/198,223, filed Jul. 17, 2002 titled, "Laminated Flow Devices"; U.S. application Ser. No. 10/273,723 filed Oct. 18, 2002 titled, "Electrokinetic Device Having Capacitive Electrodes"; U.S. application Ser. No. 10/322,083 filed Dec. 17, 2002 titled, "Electrokinetic Device Having Capacitive Electrodes" and U.S. application Ser. No. 11/112, 867 filed Apr. 21, 2005 titled, "Electrokinetic Delivery Systems, Devices and Methods," each of which are incorporated herein by reference in its entirety.

The pump element 20 is connected to supporting electronics 5 by electrical connectors 26. The supporting electronics 5 may be altered depending upon the type of pump element(s) used but will generally include a user control interface 6, electronic control circuitry 8 and a power supply 10. The user control interface 6 may be a touch screen or other input means to allow a user to operate the delivery system, select a program or otherwise provide programming instructions to the system. The electronic control circuitry contains the programming instructions needed to translate the user inputs into commands to operate the pump element. The electronic control circuitry also regulates the power supply to achieve user desired pumping characteristics such as flow rate and delivery timing. The power supply 10 may contain a battery or the delivery system may be plugged into an electrical supply. The supporting electronics are conventional and will be understood by those of ordinary skill in the art.

An exploded view of one type of pump element 20 is shown in FIG. 1B. The pump element 20 shown in FIG. 1B is an electrokinetic pump element. Electrokinetic pump element contains a porous material 22 between two capacitive electrodes 24. Illustrative electrode materials include carbon aero gel or carbon nanofoam, One example of a suitable porous membrane is a microporous filter having a pore size ranging from tens of nanometers to micron size. In one embodiment, the preferred pore size is 100-200 nanometers. The capacitive electrodes are connected to the supporting electronics 5 by electrical connectors 26. The pump element contains a pump fluid or buffer 80 that is moved through the porous material 22 from one electrode towards the other electrode depending on how voltage is applied between the electrodes 24. The electrokinetic flow produced by the pump element 20 may be in one direction (from one electrode to the other electrode) or may alternate directions of flow (towards one electrode and then away from that electrode and towards the other electrode). Examples of electrokinetic pumps configurations, electrolytes, electrodes, porous materials (also referred to as porous dielectric materials) and other details of are described in co-pending and commonly assigned patent applications: U.S. application Ser. No. 10/198,223, filed Jul. 17, 2002 titled, "Laminated Flow Devices"; U.S. application Ser. No. 10/273,723 filed Oct. 18, 2002 titled, "Electrokinetic Device Having Capacitive Electrodes"; U.S. application Ser. No. 10/322,083 filed Dec. 17, 2002 titled, "Electrokinetic Device Having Capacitive Electrodes" and U.S. application Ser. No. 11/112,867 filed Apr. 21, 2005 titled, "Electrokinetic Delivery Systems, Devices and Methods," each of which are incorporated herein by reference in its entirety.

Optionally, a storage fluid 50 fills the second chamber. The storage fluid 50 may be a fluid used to maintain the integrity of the pump element 20 during storage or prior to operation. The storage fluid 50 may be the same or different than the fluid 80 stored in the first chamber. The storage fluid 50 may also be a pump fluid (i.e., such as electrolyte suited to operation in an electrokinetic pump) moved by operation of the pump element 20. A delivery fluid 36 is stored in the third chamber 35. In some embodiments, the delivery fluid is a drug, a pharmacological or therapeutic agent, or other substance to be delivered by operation of the pump element 20. FIG. 1A also illustrates a conventional syringe 90 is also illustrated having a body 91 with a tip 92. A plunger 93 is attached to handle 95 by shaft 94 is disposed within the body 91.

Pump system 1 provides one solution to loading the pump system without the use of the pump element 20 by bypassing the pump element. Additionally, the pump element 20 remains in a fixed position within the pump housing during both filling and pumping operations. The pump systems 900 and 1000 provide an alternative apparatus and method for filling and delivering fluid. In contrast to the fixed pump element fluid system 1, the pump element in pump systems 900, 1000 moves within the pump housing during fluid delivery operations. The pump element in fluid system 1000 also moves during pump filling operations. These and other details of the pump systems 900, 1000 are described below.

Figure 2A:
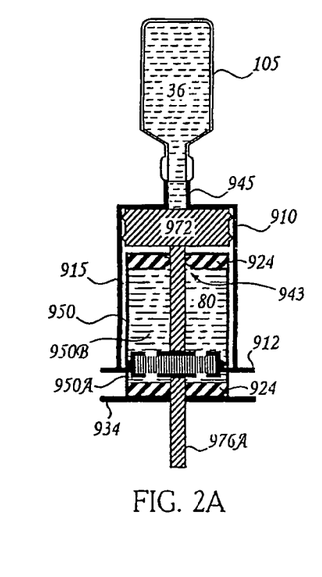
FIGS. 2A-2E illustrate details for the loading and delivery of fluid using the pumping system 900.
Figure 2B:
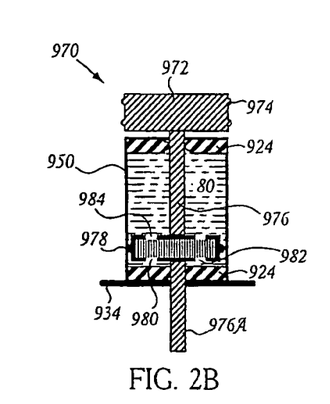
Figure 2C:
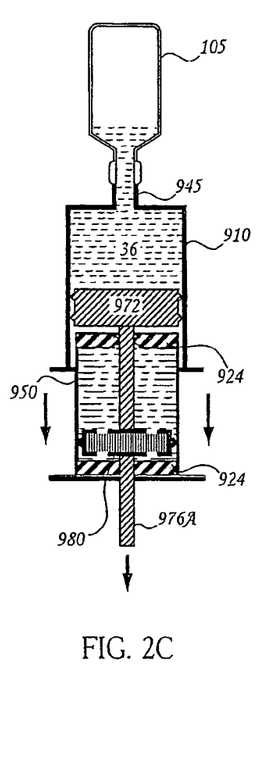
Figure 2D:
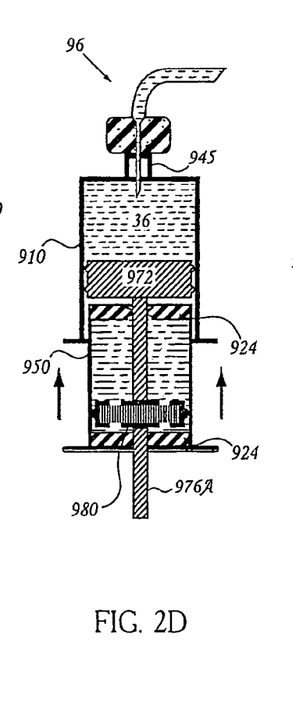
Figure 3A:
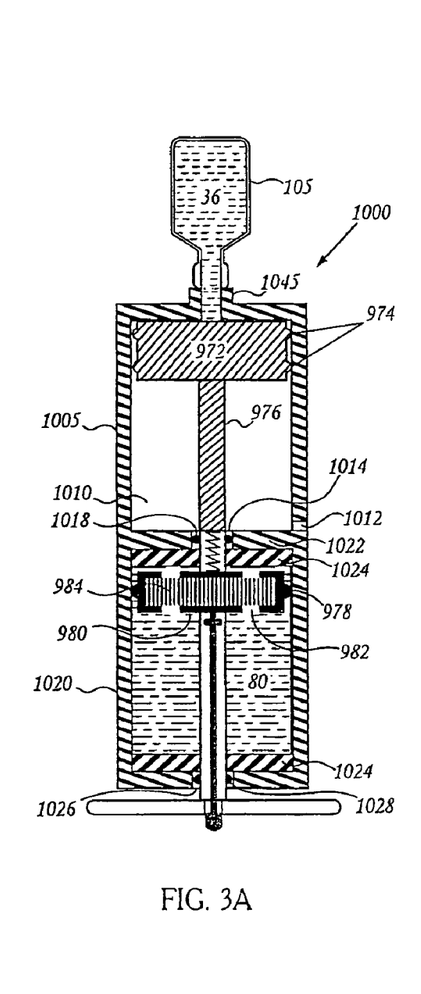
FIGS. 3A-3E illustrate details for the loading and delivery of fluid using the pumping system 1000.

FIGS. 2A-D and FIGS. 3A-E illustrate pumping systems 900, 1000. Novel piston assemblies are at the heart of the systems. The piston assemblies are designed to move within another pump component to deliver fluid. Piston assembly 970 (illustrated in FIG. 2B) and piston assembly 990 (illustrated in FIG. 3B) have several common components. A piston head 972 is connected to a housing 980 by a shaft 976. The housing 980 contains a porous material 984 and a plurality of apertures 982 allow fluid flow through the housing 980 and the porous material 984. In one embodiment, the porous material 984 is a dielectric material adapted for operation as part of an electrokinetic pump. Examples of porous dielectric materials described in the co-pending patent applications described above. A sealing element or elements 974 are provided around the perimeter of the piston head 972. The piston head 972 is sealed within a delivery chamber that is separate from the pump chamber (i.e., delivery chamber 910 in FIG. 2A) or integrally formed with the pump chamber (i.e., delivery chamber 1010 in FIG. 3A). One or more sealing elements 978 is provided around the perimeter of the housing 980. The housing 980 is sealed within the pump chamber using sealing elements 978 as shown in FIGS. 2A and 3A. Suitable materials for construction of components include polypropylene, polycarbonate and medical grade plastics.

FIG. 2A illustrates a pump 900 that includes a delivery chamber 910, a pump chamber or piston housing 950 and a wall 931 separating the pump chamber 950 from the delivery chamber 910. The piston housing 950 is filled with a suitable electrolyte 80. A piston assembly 970 has a piston head 972 in the delivery chamber 910 (i.e., outside of the pump housing 950), a housing 980 in the piston housing or pump chamber 950 and a shaft 976 connecting the piston head 972 to the housing 980. The shaft 976 passes through the wall 931 separating the pump chamber 950 from the delivery chamber 910. As shown in FIG. 2B, the housing 980 divides the piston housing 950 into a first portion 950A and a second portion 950B. A pair of electrodes 924 are in the pump housing 950 where there is one electrode 924 is on each side of the housing 980. There is an electrode 924 in the first portion 950A and an electrode 924 in the second portion 950B. In one embodiment, each electrode in the pair of electrodes has a double layer capacitance of more than $10^{-4}$ microfarad/cm$^2$. A porous material 984 is contained inside of the housing 980 and in contact with the electrolyte 80. The housing 980 has apertures 982 that provide fluid communication between the first portion 950A and a second portion 950B. The housing 980 is sealed within the piston housing 950 using sealing element 978.

The housing 910 includes an outlet 945 and an interior space 915. The interior space 915 is sized and shaped to sealingly receive the piston head 972. The piston housing 950 is adapted for pumping operations using the piston assembly 970. The housing 950 includes electrodes 924 positioned on either end of housing interior. The piston assembly 970 is disposed within the housing 950 with shaft 976 extending through a sealed opening 943. The housing 950 is inserted into the interior space 915 and the piston 972 is advanced against the interior 915 adjacent the outlet 945. The pump system 900 is now ready for filling.

The pump system 900 is filled by attaching a vial 105 or other suitable container to the outlet 945 and then withdrawing the piston housing 950 from the delivery interior 915 as indicated by the arrow in FIG. 2C. The relative movement of the pump chamber 950 to the delivery chamber 910 draws the delivery fluid 36 from vial 105 through the outlet 945 and into the interior 915 as shown in FIG. 2C. Next, the vial 105 is removed and a delivery device, such as an infusion set 96, is attached to outlet 945. An optional purge or prime procedure is illustrated in FIG. 2D. Before attachment of the delivery device, after attachment of the delivery device or both before and after attachment of the delivery device the system may be primed or purged of air by advancing the piston housing 950 relative to the delivery chamber 910 as indicated by the arrows in FIG. 2D.

Figure 2E:
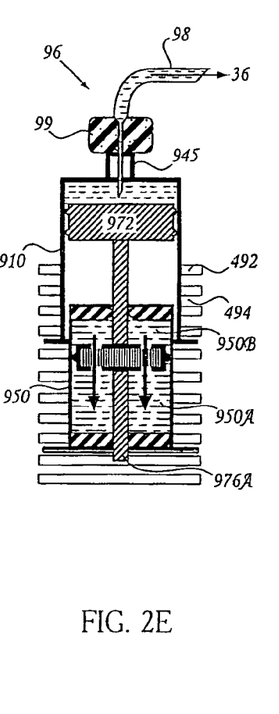

Prior to commencement of pumping, the position of the piston housing 950 is fixed relative to the delivery chamber 910. In one embodiment, the housings 910, 950 are fixed when feature 912 on delivery chamber 910 and feature 934 on chamber 950 are locked in place using bars 492 and spaces 494 within the frame 490 as illustrated in FIG. 2E.

Pumping begins when an electric field is applied across electrodes 924. Application of an electric field across the electrodes 924 moves electrolyte 80 in the pump chamber 950 from one side of the housing 980 (i.e., the portion 950B) to the other side of the housing (i.e. the portion 950A). In one embodiment, the electrolyte 80 is moved electrokineticly through the apertures 982 and the porous material 984 from one electrode 924 towards the other as indicated by the arrows in FIG. 2E. This movement of the electrolyte decreases the volume of the portion 950B and increases the volume of the portion 950A. Increasing volume of portion 950A moves the housing 980 and the piston head 972 towards the outlet 945 which in turn expels delivery fluid 36 out through outlet 945.

Figure 3B:
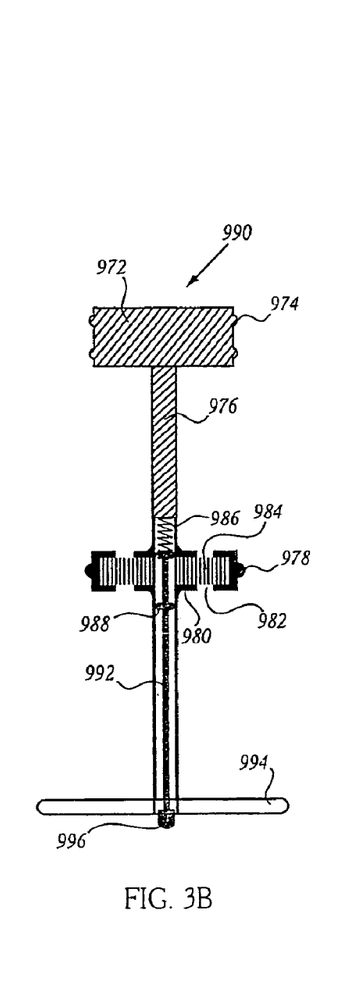

Turning now to FIGS. 3A and 3B that illustrate the pumping system 1000. The pumping system 1000 includes a delivery chamber 1010 and a pump chamber 1020 within a single housing (i.e., the pump housing 1005). The delivery chamber 1010 has an outlet 1045 and a vent 1012. A vial 105 filled with a delivery fluid 36 is attached to outlet 1045 and the pump system 1000 is ready for filling. The piston assembly 990, illustrated in FIG. 3B, is disposed within the pump housing 1005. The piston assembly 990 is arranged within a piston housing or pump chamber 1020 filled with an electrolyte 80. A housing 980 within the piston housing divides the piston housing into a first portion 980A and a second portion 980B and maintained by seals 978. The housing 980 has apertures 982 that provide fluid communication between the first portion 980A and the second portion 980B. The housing 980 contains a porous material 984 in communication with the electrolyte 80. The porous material 984 may be a porous dielectric material adapted for operation as part of an electrokinetic pump. A pair of electrodes 1024 are provided in the pump chamber 1020. One electrode 1024 is provided on each side of the housing 980 (i.e., one electrode in the first portion 980A and one electrode in the second portion 980B). In the illustrated embodiment, the electrodes, dielectric material and electrolyte are selected to provide electrokinetic movement of the electrolyte within the pump chamber and through the housing 980. In one embodiment, the electrodes are made of a material having a double layer capacitance greater than $10^{-4}$ microfarads/cm$^2$.

A shaft 976 connects the housing 980 to a moveable pump element (here, a piston head 972) and a handle 994 outside of the piston housing 1020. The shaft 976 may be a single piece as illustrated or be formed of multiple pieces. An example of a multiple piece shaft would be a first shaft connecting the housing 980 to the piston head 972 and a second shaft connecting the housing 980 to the handle 994. Sealing elements 1018, 1028 maintain the fluid integrity where the shaft passes through the pump chamber walls via openings 1014, 1026. The piston assembly 990 also includes a bypass feature not found in piston assembly 970. The piston assembly 990 includes a valve 988 within the shaft 976 that provides a fluid pathway from one side of the housing 980 (i.e., the first portion 980A) to the other side of the housing 980 (i.e., the second portion 980B) without passing the fluid through the porous material 984. The valve 988 or fluid path through the shaft 976 provides a bypass through the porous material contained in the housing without requiring operation of the electrodes or inducing flow though the material 984. The valve 988 is actuatable from a handle 994 attached to the housing 980. In the illustrated embodiment, a button 996 located on the handle 994 is used to depress the spring in 986, open valve 988 and to allow fluid flow through the shaft 976 around the housing 980.

Figure 3C:
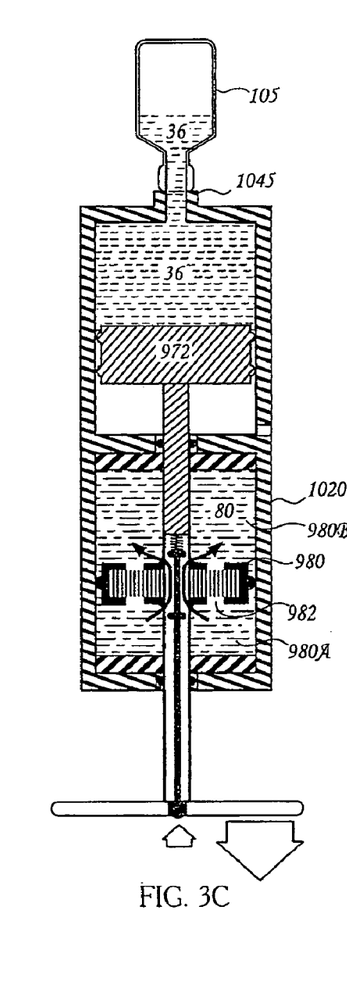

FIG. 3C illustrates a method of operating a fluid delivery system 1000 having a pump chamber 1020 and a delivery chamber 1010. Filling is performed by withdrawing the shaft 976 within the fluid delivery assembly to simultaneously displace a moving pump element within the pump chamber (i.e., the piston head 972) and bypass fluid around the housing 980 in the pump chamber 1020 (as shown by the arrows in pump chamber 1020). FIG. 3C also illustrates that the button 996 in handle 994 is depressed (thereby opening the bypass with valve 988) while the handle 994 is withdrawn. Once a vial 105 or other suitable container is attached to the outlet 1045, withdrawing the shaft 976 from the pump assembly 1045 also introduces the delivery fluid 36 into the delivery chamber 1010 and into contact with the moveable pump element (i.e., the piston head 972). When the button 996 is depressed the bypass valve 988 allows fluid allows buffer 80 to pass from one side of the housing 980 to the other side as illustrated by the arrows. Now that buffer 80 may move freely within the pumping chamber 1020, the handle 994 is withdrawn thereby withdrawing piston head 972 within the delivery chamber 1010. This action draws delivery fluid 36 into the delivery chamber the outlet 1045.

Figure 3D:
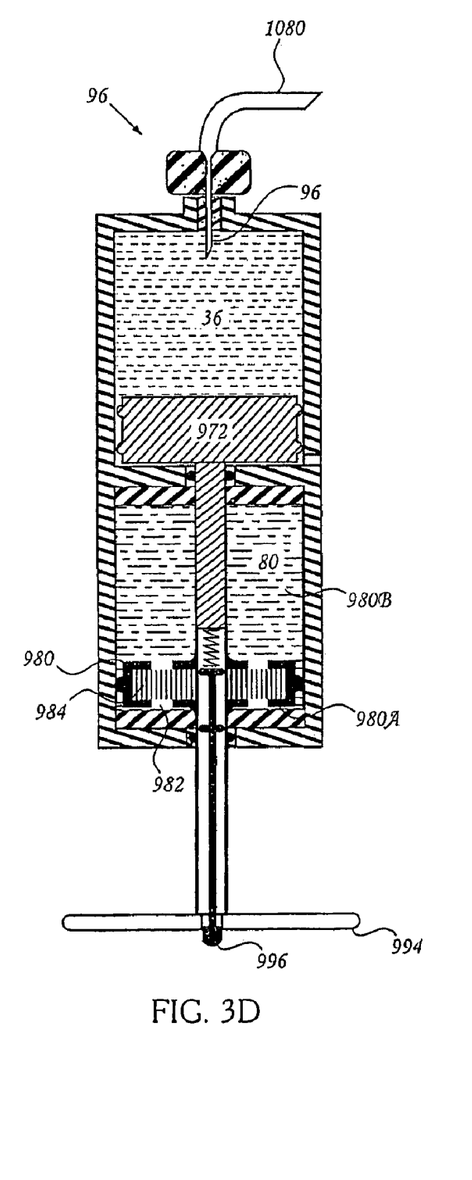

As shown in FIG. 3D, when the filling operation is complete, the button 996 is released. When button 996 is released, action by spring 986 forces the valve 988 closed thereby preventing further passage of buffer 80 through the bypass valve as illustrated in FIG. 3D. A delivery device is attached to the outlet 1045. In the illustrated embodiment, the delivery device is an infusion set 96 having an outlet or conduit 1080.

Figure 3E:
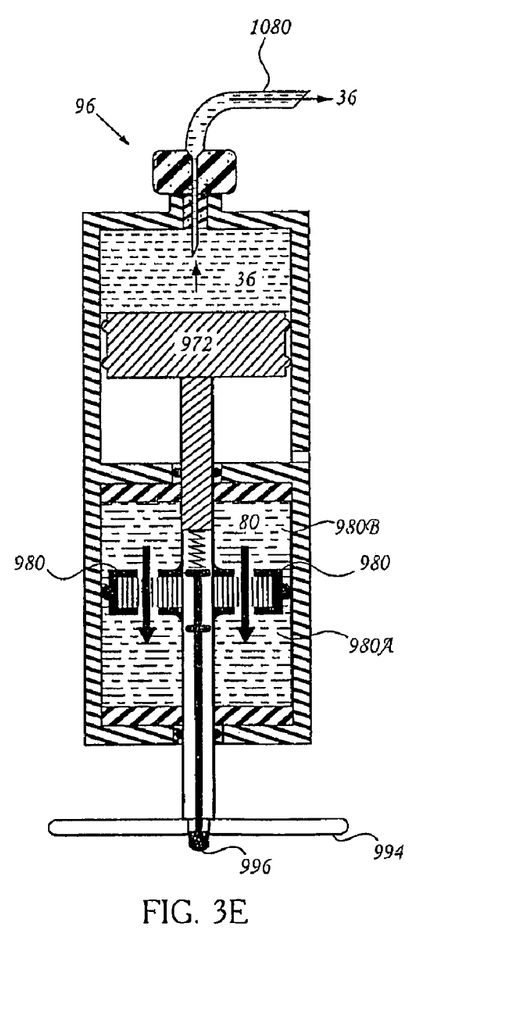

Pumping begins with the application of an electric field across the electrodes 1024 that moves the electrolyte 80 in the pump chamber from one side of the housing 980 to the other as indicated by the arrows inside chamber 1020 in FIG. 3E. The movement of electrolyte from portion 980B into 980A moves the housing 980 and the piston head 972 towards the outlet 1045 by increasing the volume of portion 980A while decreasing the volume of the portion 980B. In the illustrated configuration, when an electric field is applied across electrodes 1024, electrolyte 80 is moved electrokineticly through the apertures 982 and the porous material 984 from one electrode 1024 towards the other electrode 1024 as indicated by the arrows inside chamber 1020. As such, movement of the buffer 80 through the apertures 982 moves the housing 980. Movement of the housing 980 in turn advances the piston head 972 to expel delivery fluid 36 out through outlet 1045 and delivery device 96.

Figure 4:
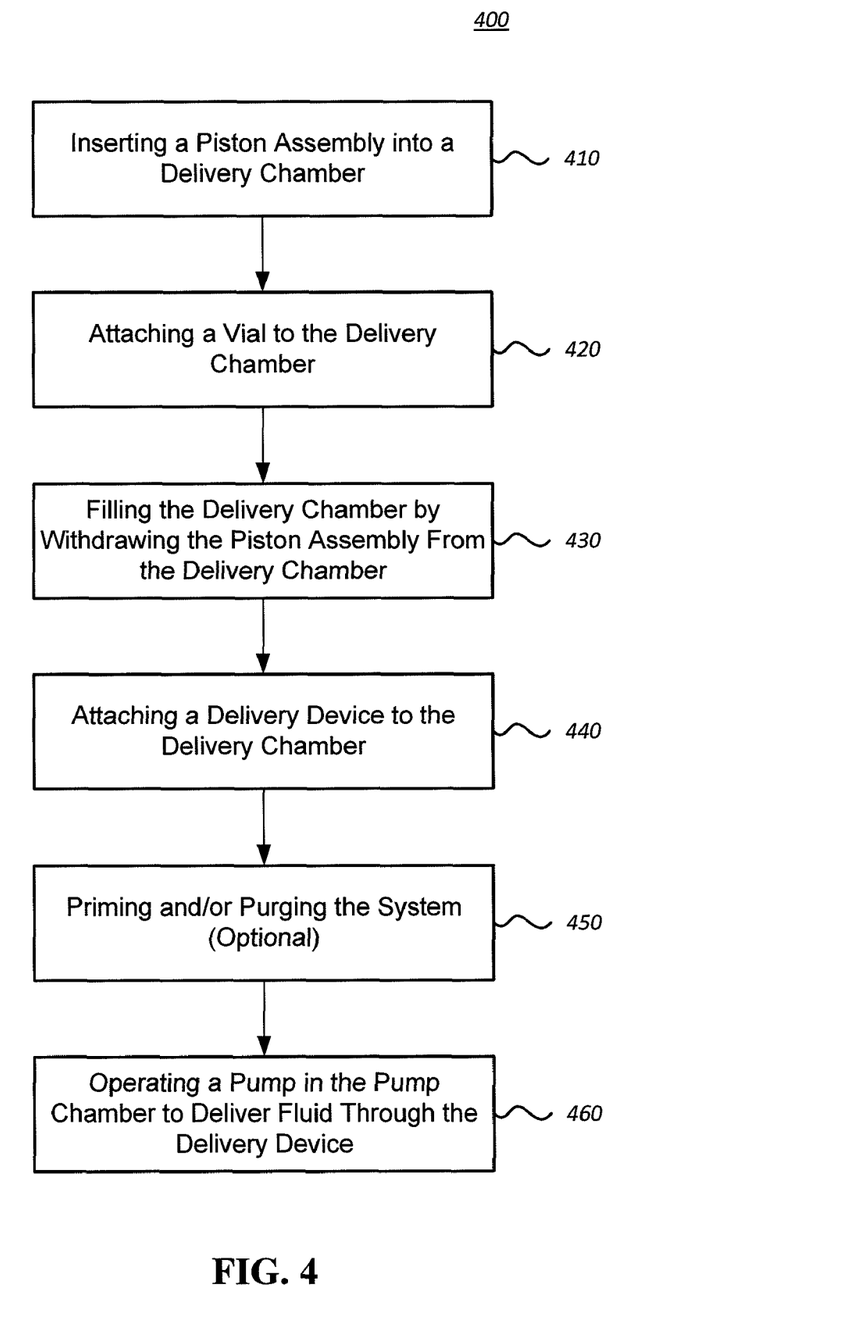
FIG. 4 illustrates a method of fluid delivery.

FIG. 4 illustrates a flow chart 400 depicting an exemplary fluid delivery method. First, at step 410, the step of inserting a piston assembly into a delivery chamber. By way of non-limiting examples, this step is illustrated and described with regard to FIGS. 2A and 3A. Next, at step 420, the step of attaching a vial to a delivery chamber. By way of non-limiting examples, this step is illustrated and described with regard to FIGS. 2C and 3C. Next, at step 430, is the step of filling the delivery chamber by withdrawing the piston assembly from the delivery chamber. By way of non-limiting examples, this step is illustrated and described with regard to FIGS. 2C, and 3C. The next step, step 440, is the step of attaching a delivery device to the delivery chamber. By way of non-limiting examples, this step is illustrated and described with regard to FIGS. 2D and 3D. Optionally, before or after attaching the delivery device, the system may be primed or purged (step 450) as shown and described, for example, with regard to FIG. 2D. Finally, step 460, the step of operating a pump in the pump chamber to deliver fluid through the delivery device. By way of non-limiting examples, this step is illustrated and described with regard to FIGS. 2E, and 3E.

The foregoing illustrative embodiments have used certain terms to provide an explanation of the principal involved or operation of the illustrated systems. It is to be appreciated that numerous alternatives for components and elements are possible. For example, the pump element and components in the pump chamber may form an electrokinetic pump as described but may be reconfigured to accommodate the use of diaphragm pumps, piston pumps, and piezoelectric pumps. The supporting electronics 5 and electrical connectors 26 would be modified as needed according to the type of pump element and other components used. Additionally, many of the illustrative configurations described the use of a movable pump element such as piston head 972. It is to be appreciated that the movable pump element may be a piston or a diaphragm and that both may be used in a single system (i.e., as illustrated in FIG. 1A). The diaphragm may be a 'rolling' type diaphragm. Rolling diaphragms have a convolute that allows predictable travel of the diaphragm. While a rolling diaphragm does have advantages, the invention is not so limited and other types of diaphragms and moveable pump elements may be used.

The process of drug aspirating and air purging has been shortened in many of the illustrative descriptions. For configurations describing filling the pump with delivery fluid, the description simply indicates to pull back on a handle or pump housing to drawn drug or delivery fluid in. Those of ordinary skill will appreciate that this is an abbreviated instruction. Like any drug aspiration process, trapped air is vented before the drug is delivered. As such, the full process includes drawing drug in by pulling back on the handle or housing, then while holding the unit with the drug exit port at the top, flick the unit to release bubbles, and then press the syringe handle in to purge air out of the unit. The process is repeated if necessary until all visible air is removed and the unit is filled with the desired amount of drug. This process is identical to the typical method used by medical practitioners to aspirate drug into syringes and purge air.

A generic infusion set 96 is described and many of the pump system embodiments are represented as connected to an infusion set. While not illustrated in every embodiment, a similar configuration of an infusion set connection or other suitable delivery device can be inferred for all pump system embodiments. Alternatively, the delivery fluid 36 or drug may be dispensed without an infusion set such as, for example, when it is delivered directly into a cannula or elsewhere.

The use of liquid and/or air seals have been illustrated in some embodiments. In some embodiments, those components requiring seals (piston head 972, housing 980, etc.) have two o-ring seals while in other embodiments only one o-ring seal shown. Two seals are typically used in medical syringes and have thus been shown in pairs on most of the pistons described herein. It is to be appreciated that one or more o-rings may be used, however, or alternate types of seals may be employed. O-rings may be made from conventional sealing materials suited to medical application such as silicone and urethane, for example Any of the configurations may be partially filled with drug or delivery fluid to any desired amount. Additionally, in some embodiments, the portion of pump housing (i.e. delivery chambers 910, 1010) that stores the delivery fluid would be transparent and graduated to allow visibility and amount of the delivery fluid 36 present. In addition, a transparent housing generally would also allow visibility of any air that needs to be purged during the filling process. Volumetric increment markings may also be appropriately provided on the pump housing by printing, stamping, embossing, painting or otherwise indicating the contents of the delivery fluid 36 within a drug or delivery chamber. Suitable materials for construction of components include polypropylene, polycarbonate and medical grade plastics.

One benefit of the pumping systems described herein is that these systems provide indirect pumping of delivered liquids regardless of the type of pump used for pump element 20 or pumping configuration. The pump components are contained within piston housing 950 or pump chamber 1020 and as the descriptions above make clear, the delivery fluid 36 does not pass through any pump mechanism and is actually separated from the pump components. Another advantage is the decreased likelihood of damage to fluids that are susceptible to mechanical and/or chemical degradation such as long chain protein molecules and peptides. Mechanical actions including compression, shearing, and extrusion, as well as exposure to electrical currents can cause molecular level damage to some fluids. By obviating the need for the fluids to pass through the pump mechanism, concern over pumping damage to these compounds is diminished.

The term buffer has been used throughout the description. Buffer refers to any suitable working fluid that may be used by a particular pumping system. In many pumping system embodiments, the buffer or working fluid is any fluid having a viscosity low enough to be pumped through the pump element. In those embodiments where the pump element is an electrokinetic pump, working fluid is an electrolyte suited to the specific electrodes and dielectric material used by the electrokinetic pump. In one specific embodiment, the electrolyte is a buffered electrolyte. One buffered electrolyte is a buffer made from TRIS [tris(hydroxymethyl)aminomethane] and sorbic acid at a concentration of 10 Mm and a pH of 8.3. Other common buffer ions work as well. For example, TRIS-HCL, borate or sodium acetate buffers can be used. The buffer may also include other additives such as preservatives.

The term delivery fluid has been used throughout the description. In many pumping system embodiments, the delivery fluid is any fluid having a viscosity low enough to be pumped through action of the pump element. In some embodiments, the delivery fluid is a pharmacological agent. In other embodiments, the delivery fluid is a therapeutic agent. In still other embodiments, the delivery fluid is a saline solution or Ringers solution.

While numerous embodiments of the present invention have been shown and described herein, one of ordinary skill in the art will appreciate that such embodiments are provided by way of example only. Numerous variations, changes, and substitutions will now occur to those skilled in the art without departing from the invention. In addition, the intended uses of the present invention include a variety of medical applications as well as other applications where highly precise, compact devices for fluid transport are needed. It should be understood that various alternatives to these embodiments of the invention described herein may be employed in practicing the invention. It is intended at the following claims defined the scope of the invention and it methods and structures within the scope of these claims and their equivalents be covered thereby.

What is claimed is:
1. A piston assembly, comprising:
   a piston housing;
   a material housing within the piston housing that divides the piston housing into a first portion and a second portion, the material housing having apertures that provide fluid communication between the first portion and the second portion;
   a porous material inside of the material housing;
   a first shaft connecting the material housing to a piston head outside of the piston housing;
   a second shaft connecting the material housing to a handle outside of the piston housing; and
   a valve within the second shaft, wherein actuation of the valve provides a flow path between the first portion and the second portion, and wherein the flow path includes a bypass through the porous material contained in the material housing.

2. The piston assembly of claim 1 wherein the piston housing is filled with an electrolyte.

3. The piston assembly of claim 2 wherein the porous material inside of the material housing is in contact with the electrolyte.

4. The piston assembly according to claim 1 wherein the porous material is a porous dielectric material adapted for operation as part of an electrokinetic pump.

5. The piston assembly according to claim 1 further comprising a sealing element around the perimeter of the piston head.

6. The piston assembly according to claim 1 wherein the valve is actuatable from a handle attached to the second shaft.

7. The piston assembly according to claim 1 further comprising a sealing element around the perimeter of the material housing that seals the material housing to a wall of the piston housing.

8. The piston assembly according to claim 1 further comprising an electrode in the first portion and an electrode in the second portion.

9. The piston assembly according to claim 8 wherein the electrodes have a double layer capacitance of greater than $10^{-4}$ microfarad/cm$^2$.

10. A pump, comprising:
a delivery chamber, a pump chamber and a wall separating the pump chamber from the delivery chamber; and
a piston assembly having:
a piston head in the delivery chamber;
a material housing in the pump chamber, wherein the material housing divides the pump chamber into a first portion and a second portion;
a shaft connecting the piston head to the material housing and passing through the wall separating the pump chamber from the delivery chamber;
a bypass valve in the shaft that provides a fluid pathway between the first portion of the pump chamber and the second portion of the pump chamber; and
a dielectric material in the material housing.

11. The pump according to claim 10 further comprising a pair of electrodes in the pump housing, wherein one electrode is on each side of the material housing.

12. The pump according to claim 10 further comprising apertures in the material housing that provide fluid communication between the first portion and the second portion.

13. The pump according to claim 11 wherein each electrode in the pair of electrodes has a double layer capacitance of more than $10^{-4}$ microfarad/cm$^2$.

14. The pump according to claim 10, wherein the delivery chamber is filled with an electrolyte.

15. The pump according to claim 14, wherein the dielectric material is in contact with the electrolyte.

16. The pump according to claim 10, wherein the dielectric material is a porous material adapted for operation as part of an electrokinetic pump.

* * * * *